US005683421A

United States Patent [19]

Guarini, Jr. et al.

[11] Patent Number: 5,683,421

[45] Date of Patent: Nov. 4, 1997

[54] TEETHING APPARATUS

[76] Inventors: Edward A. Guarini, Jr., 22155 Woodset La., Boca Raton, Fla. 33428; John M. Miller, 105 Sunset Dr., Cocoa Beach, Fla. 32931

[21] Appl. No.: 503,514

[22] Filed: Jul. 18, 1995

[51] Int. Cl.[6] .............................. A61J 17/00; A61M 7/00

[52] U.S. Cl. .............................. 606/235; 601/142; 601/72

[58] Field of Search .............................. 606/234–236; 601/70–80, 139–142, 2

[56] References Cited

U.S. PATENT DOCUMENTS

| | | | |
|---|---|---|---|
| 3,115,139 | 12/1963 | Schneider | 606/235 |
| 4,718,876 | 1/1988 | Lee | 446/295 |
| 5,004,473 | 4/1991 | Kalantar | 606/234 |
| 5,551,952 | 9/1996 | Falgout | 606/235 |

*Primary Examiner*—Glenn Dawson
*Attorney, Agent, or Firm*—John M. Miller

[57] ABSTRACT

An improved teething apparatus that mechanically aids in massaging and cleaning the gums and teeth of an infant. The apparatus has a flexible outer shell which covers a relatively rigid inner member. Mounted to the inner member is a motor and at least one switch which actuates the motor thereby generating vibrational forces which are transmitted throughout the inner member and outer shell. The vibrational forces soothe sore gums and facilitate in the process of breaking the cusp tips of new teeth through the gum line and aid in keeping the teeth and gum line clean.

19 Claims, 3 Drawing Sheets

TEETHING APPARATUS

BACKGROUND OF THE INVENTION

1. Field of the Invention

The present invention relates generally to an improved teething apparatus, and in particular to a teething apparatus that vibrates to clean and massage the teeth and gums of an infant or small child thereby alleviating discomfort associated with teething and promoting good oral hygiene.

2. Description of the Prior Art

Each year millions of infants throughout the world are born. Barring abnormalities, all of them will go through the painful teething period wherein their first set of teeth break through the gum line. In order to alleviate the pain associated with teething the prior art is replete with teething devices having different shapes and surface textures. However, none of them provide an electro-mechanical means for aiding in the teething process.

A first teething device is shown in U.S. Pat. No. 1,826,943, which discloses a unitary piece of rubber comprising two ends, either end of which acts as a handle in the manipulation of the device. On opposing sides of the device are formed a plurality of spaced, nipple-like projections or stipules that are formed about the entire opposite surface which aid in massaging an infant's gums. Another teething device is shown in U.S. Pat. No. 2,826,201, issued to Yoder. Yoder discloses a teething device comprising a body of resilient material having a cavity formed therein. In use, a piece of confection is mounted within the cavity which is exposed through an opening in the cavity wall, the confection being held in place by opposed bosses of reduced thickness.

U.S. Pat. No. 3,669,117, issued to Herbert, discloses a combination teether and pacifier in the form of a thin-walled, flexible body having a nipple, guard, and teething portions which are hollow and in communicating relation with each other. A soft, compressible body of gel or liquid fills the hollow portions and the device and its compressible contents are adapted to be cooled before use to attain maximum soothing effects for the user. Yet another combination is disclosed in U.S. Pat. No. 5,048,143, issued to Carol, which discloses a combination toothbrush and teething device having a body in the shape of a closed ring with a forward curved portion sized to fit within a child's opened mouth. A rearward curved portion forms a handle for gripping by a child; a brush head forms a plurality of upstanding flexible bristles extending from the forward curved portion of the body. To facilitate teething, a plurality of protruding teething bumps may be located on the rearward portion of the body for biting engagement with the child's teeth and gums.

Although there are several different prior art teething devices, nowhere is there a teething apparatus that electro-mechanically aids in the massage of an infant's gums and teeth. Accordingly, there is a need for an improved teething apparatus that vibrates and massages the gums of the infant to alleviate the discomfort associated with teething.

SUMMARY OF THE INVENTION

The improved teething apparatus of the present invention solves the need present in the prior art by the provision of a teething apparatus that comprises an outer jacket which houses a means for massaging connected to at least one switch. When the at least one switch is actuated, the means for massaging vibrates and thereby massages the gums and teeth of a child.

It is a principal object of the invention to provide a device which will materially assist in the teething process by electro-mechanically aiding in massaging the gums of the child.

It is an additional another object of the present invention to provide a vibrating teething apparatus that soothes soreness associated with teething.

It is yet another object of the present invention to provide a vibrating teething apparatus that assists in cleaning an infant's teeth.

In accordance with these and other objects which will become apparent hereinafter, the instant invention will now be described with particular reference to the accompanying drawings.

DESCRIPTION OF THE PREFERRED EMBODIMENTS

Figures 1, 2, 3:
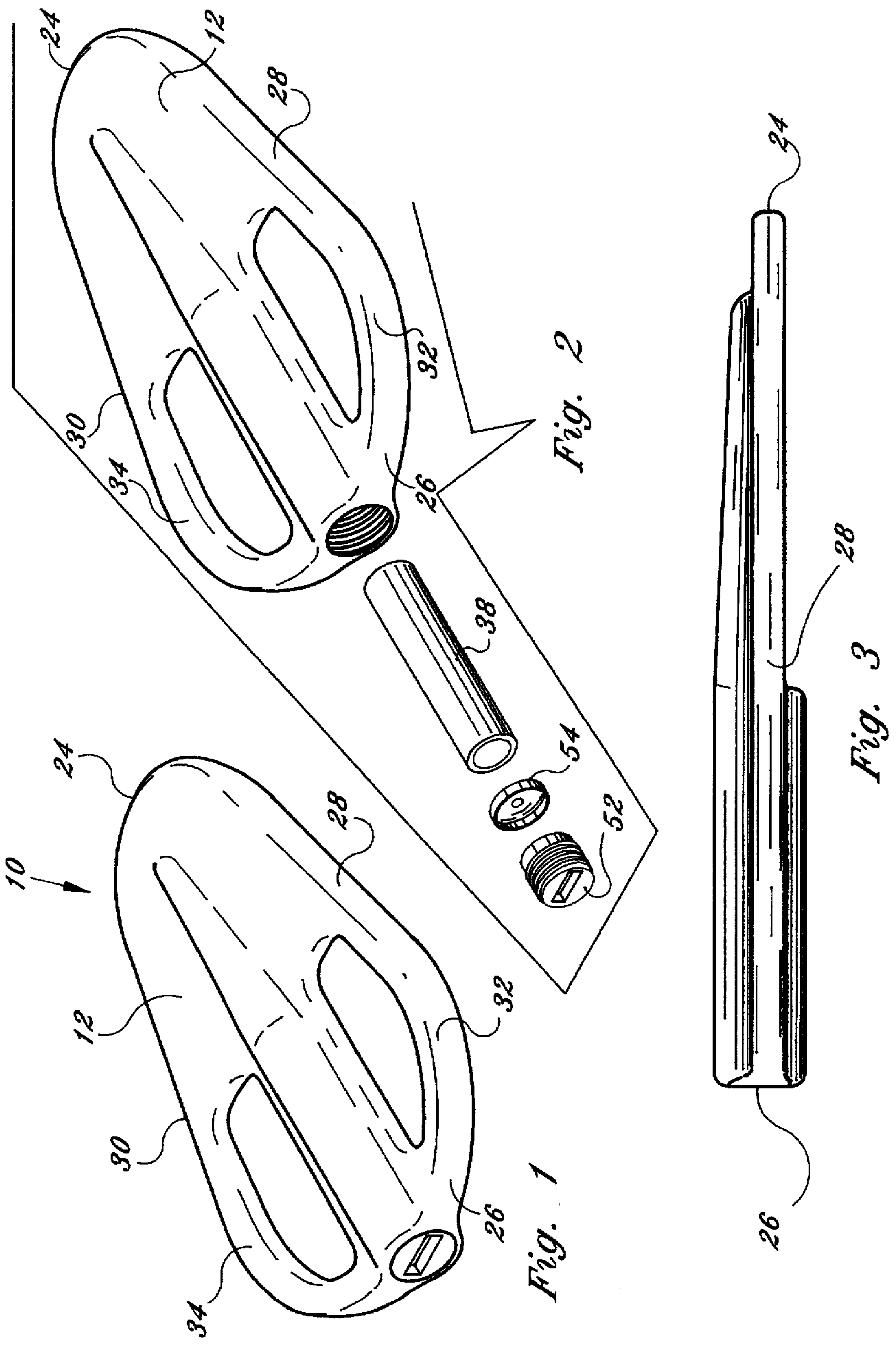
FIG. 1 is a perspective view of the present invention.
FIG. 2 is an exploded view of the present invention.
FIG. 3 is a side elevational view of the present invention.

With reference to FIGS. 1–6 there is depicted an improved teething apparatus generally referenced by numeral 10. The teething apparatus 10 generally comprises a outer jacket 12, inner member 14, motor 16 with offset 18, at least one switch 20, and battery compartment 22.

As shown in FIG. 1 the outer jacket 12 is formed with curved and rounded edges so that no sharp angles are introduced to the infant's or child's soft tissue when the teether apparatus is in use. Typically, a child's mouth will be approximately 1½" wide and approximately 2" in depth. Accordingly, in the preferred embodiment the improved teething apparatus 10 will have a forward curved portion 24 approximately 1¼" wide and rearward curved portion 26 approximately 2" wide. Sides 28 and 30 space the forward portion 24 from the rearward portion approximately 4". Additionally, apparatus 10 has a height less that its legnth and width in the plane of inner member 14. Also, in one embodiment the interior member is parallel with a plane formed by elongate axes of the apparatus. In the preferred embodiment the outer jacket 12 is comprised of a silicon rubber. However, it recognized that latex rubber, foamed elastomers or other material with rubber like physical properties may be used.

Figure 4:
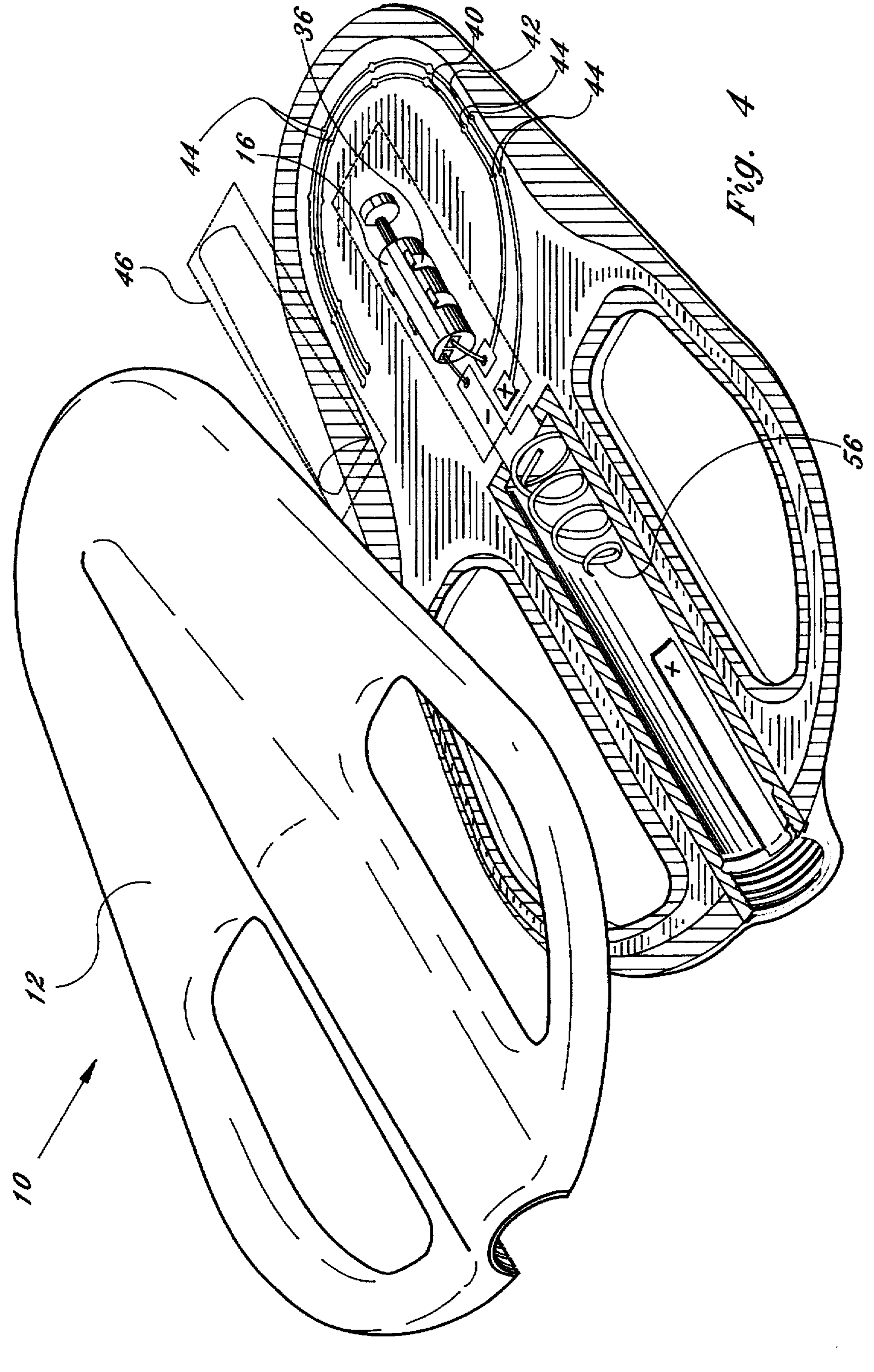
FIG. 4 is an exploded sectional view of the present invention.
Figure 5:
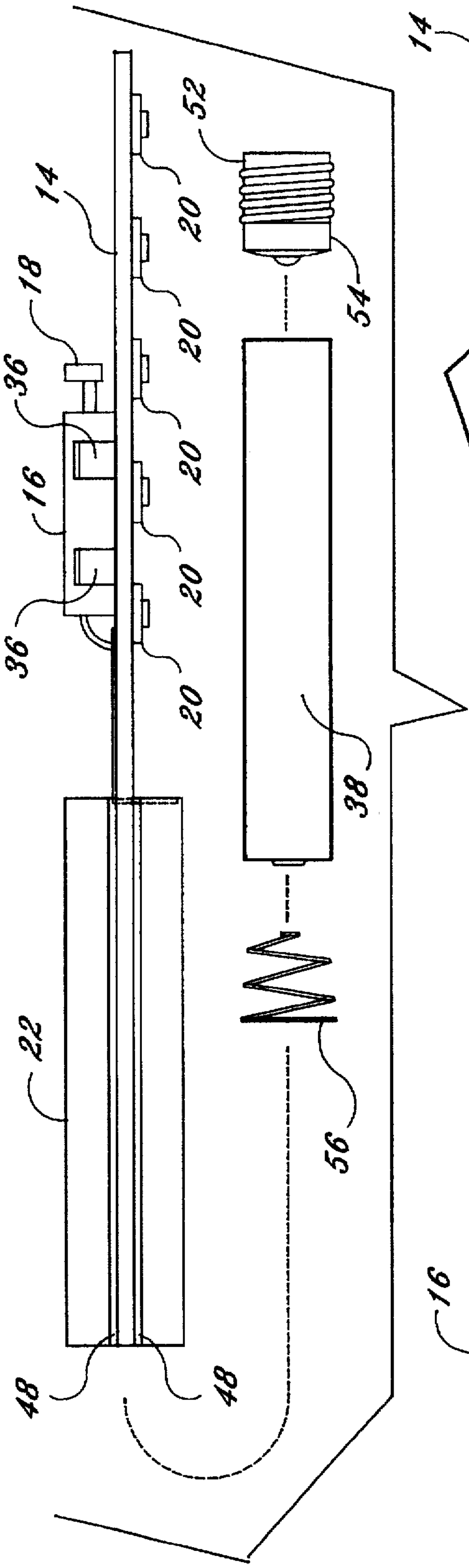
FIG. 5 is a side elevational view of the inner member and battery compartment of the present invention.
Figure 6:
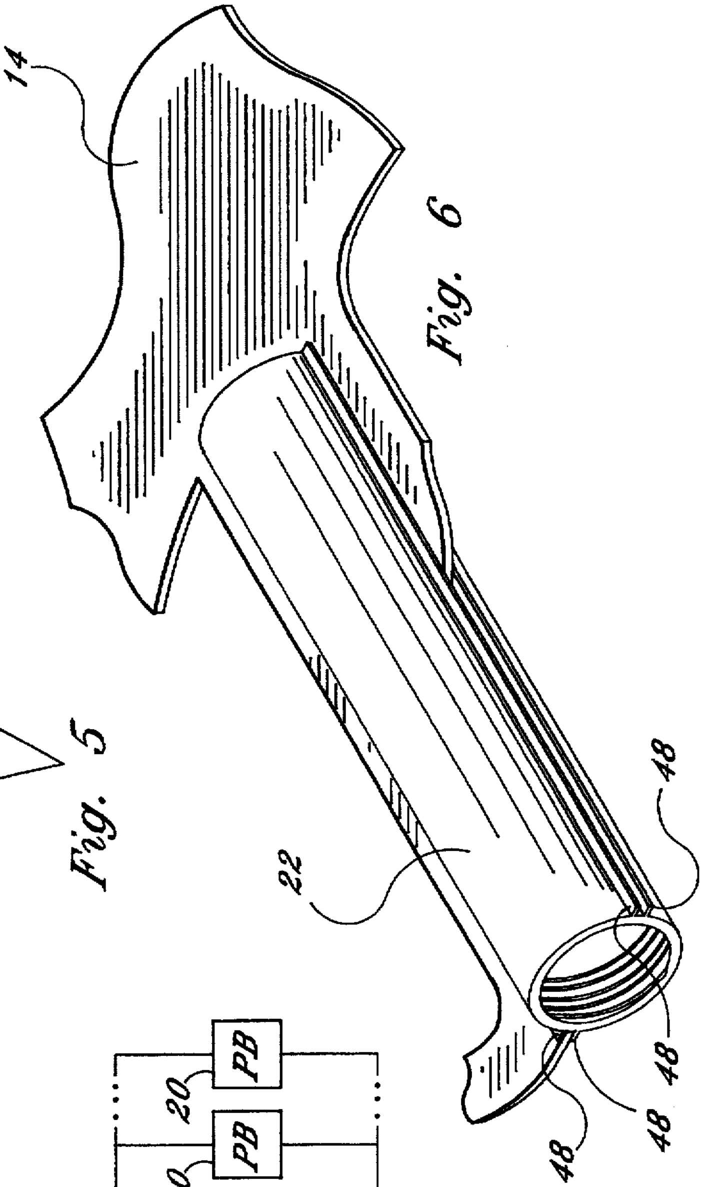
FIG. 6 is a partial view of the battery compartment and inner member of the present invention.

FIGS. 4–6 depict inner member 14 of the preferred embodiment. As shown in the figures, inner member 14 is cut such that it is of the general shape of the apparatus 10. Additionally, inner member 14 is cut such that handles 32 and 34 are formed near the rearward curved portion of the apparatus. Accordingly, in use, a child can grasp handles 32–34 to direct forward curved portion 24 into their mouth.

Inner member 14 serves as a mounting surface for electrical components as well a surface for electrical connections. Additionally, member 14 serves as a conduit for the vibrational forces that are generated by motor 16 as described below. Preferably, inner member 14 is a printed circuit board (PCB) having through holes which aid in the electrical connection of devices mounted on the board. Circuit pathways 40–42 and soldering pads are etched on the PCB such that battery 38, motor 16 and switches 20 are electrically connected. It is realized, however, that inner member 14 can be any semi-rigid material such as plastic upon which electrical components can be mounted and through which vibrational forces can be transmitted.

FIGS. 4 and 5 depict the motor 16, at least one switch 20 and a battery storage compartment 22 which are mounted to inner member 14. Preferably, motor 16 is centrally mounted via clips 36 to inner member 14 such that vibrational forces are evenly transmitted throughout the device. Also shown in FIG. 4 is a motor cover 46 (shown in phantom by dot-dashed lines) that prevents outer jacket 12 from interfering with the motor and offset.

In order to generate the vibrational force, motor 16 has an eccentrically configured offset 18 connected to its shaft. Accordingly, rotation of the shaft creates an uneven torque that results in vibration of motor. In turn, the vibration is transmitted to the inner member 14 and outer jacket 12 where it ultimately aids in massaging the gums and teeth of an infant.

Figure 7:
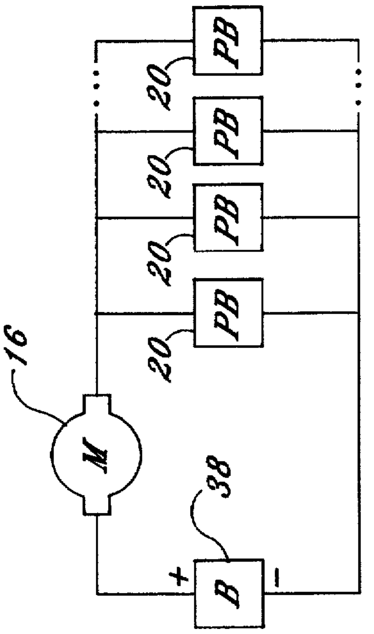
FIG. 7 is an schematic diagram of the electric circuit of the present invention.

Motor 16 is preferably a DC motor which is electrically connected with at least one switch 20 to a power source such as a battery for example. In the preferred embodiment, there are a plurality of push button switches 20 mounted on inner member 14 beneath the outer jacket 12 in the forward curved portion 24 of teether 10. Switches 20 have a low profile and are of the normally open momentary contact type. When several switches are used they are connected in parallel as shown in FIG. 7 such that the actuation of any one switch will electrically connect the motor with battery 38 or alternate power source. As shown in FIG. 5 switches 20 are mounted to the underside of the PCB proximal to forward curved portion 24, although it is realized the switches can be located anywhere on the apparatus. Switches 20 comprise two electrical contacts which pass through holes in the PCB where they are coupled to circuit pathways 40 and 42 via soldering. Small solder bumps 44 shown in FIG. 4 illustrate the connection between push-button switches 20 and circuit pathways 40 and 42.

In an alternate embodiment, switches 20 can be supplemented or replaced with a single pole slide switch (not shown). In this embodiment, when the switch is slid to the on position the motor is continuously activated until the switch is slid to the off position. This feature may be used in teaching the infant that the apparatus vibrates or until the infant learns to teeth on the device to activate switches 20.

As shown in FIG. 6, battery compartment 22 has runners 48 along its outside surface that permit the compartment to be slid onto a rectangular notch cut in inner member 14 as shown in FIG. 6. It is realized however that battery compartment 22 and inner member 14 may be formed of a single piece of plastic for ease in manufacturing and such an embodiment is considered to be within the scope of this invention. Within compartment 22 is a conventional spring 56 that make electrical contact with battery 38 and electrically connects the negative side of the battery with the negative lead of motor 16. In an alternate embodiment, at least one of the switches 20 can be a slide type switch that remains closed once actuated until the switch is manually opened.

Cap 52 is threaded to engage the threads on the inner surface of compartment 22 as shown in FIGS. 2, 4 and 6. Additionally, cap 52 is equipped with a conductive sleeve 54 that makes contact with an opposing end of battery 38 and conductor 60 when the cap is screwed into compartment 32. Conductor 60 travels down the inner length of compartment 22 and penetrates the side wall and is eventually connected to the positive side of switches 20 through circuit pathway 42.

In use, a child or infant grasps handles 32–34 and directs forward curved portion 24 into his/her mouth. Thereafter, teething on outer jacket 12 of the apparatus will depress the surface of the jacket and subsequently depress at least one of the switches 20 thereby completing the electrical circuit between the motor and the battery 38 which causes the motor to rotate. In turn, vibrational forces created by the motor and offset are transmitted throughout inner member 14 and outer jacket 12 to the infant's teeth and gums.

The teething apparatus 10 may be effectively used by an infant prior to the eruption of his teeth. In this case, the massaging effect is believed to help alleviate the discomfort associated with teething and help the teeth to pierce through the gum line. Additionally, it is believed that outer jacket 12 in conjunction with the massaging action assists the infant in forcing the cusp tips of the teeth through the soft tissue of the gums.

It is also believed that the massaging action helps loosen food particles that are attached to an infant's teeth. The teeth of small children have grooves on the top which provide areas where food particles may build up. This food can lead to plaque which needs to be removed from the teeth even as they erupt. If the plaque is left on the teeth for an extended period of time it will result in cavities along the areas where the soft tissue meets the teeth. The massaging action of the apparatus aids in loosening food particles to keep teeth clean.

The instant invention has been shown and described herein in what is considered to be the most practical and preferred embodiment. It is recognized, however, that departures may be made therefrom within the scope of the invention and that obvious modifications will occur to a person skilled in the art.

What we claim is:

1. An improved teething and cleaning apparatus, comprising:

a printer circuit board defining a handle and a curved extension;

a flexible outer jacket substantially surrounding and coupled to said printer circuit board;

means for producing vibrational forces coupled to the printed circuit board; and means for actuating said means for producing vibrational forces, said means for actuating coupling said means for producing vibrational forces to a power source when actuated.

2. The improved teething and cleaning apparatus as set forth in claim 1, wherein said printed circuit board formed from plastic.

3. The improved teething and cleaning apparatus as set forth in claim 1, wherein said outer jacket is formed from a foamed elastomer.

4. The improved teething and cleaning apparatus as set forth in claim 1, wherein said outer jacket is formed from silicone rubber.

5. The improved teething and cleaning apparatus as set forth in claim 1, wherein said means for producing vibrational forces is an electric motor and offset and said means for actuating is at least one electric switch.

6. The improved teething and cleaning apparatus as set forth in claim 5 wherein said at least one electric switch is a normally open momentary contact type switch.

7. The improved teething and cleaning apparatus as set forth in claim 5 wherein said at least one switch is a single pole single throw type switch.

8. The improved teething and cleaning apparatus as set forth in claim 5 wherein said at least one switch comprises both at least one normally open momentary contact type switch and at least one single pole single throw type switch.

9. An improved teething and cleaning apparatus, said apparatus comprising:

a planar rigid interior member defining a handle and a tongue shaped portion;

a flexible outer jacket substantially surrounding and coupled to said interior member, said outer jacket sized to enter the mouth of a child;

means for producing vibrational forces coupled to said interior member; and means for actuating said means for producing vibrational forces, said means for actuating coupling said means for producing vibrational forces to a power source when actuated;

wherein, in use, said infant teethes on said outer jacket causing said means for actuating to actuate said means for producing vibrational forces.

10. The improved teething and cleaning apparatus as set forth in claim 9, wherein said inner member is a printed circuit board.

11. The improved teething and cleaning apparatus as set forth in claim 9, wherein said inner member formed from plastic.

12. The improved teething and cleaning apparatus as set forth in claim 9, wherein said outer jacket is formed of a foamed elastomer.

13. The improved teething and cleaning apparatus as set forth in claim 9, wherein said outer jacket is formed of silicone rubber.

14. The improved teething and cleaning apparatus as set forth in claim 9, wherein said means for producing vibrational forces is an electric motor coupled to an offset and said means for actuating is at least one electric switch.

15. The improved teething and cleaning apparatus as set forth in claim 14, wherein said at least one electric switch is a normally open momentary contact type switch.

16. The improved teething and cleaning apparatus as set forth in claim 14, wherein said at least one switch is a single pole single throw type switch.

17. The improved teething and cleaning apparatus as set forth in claim 14, wherein said at least one switch comprises both at least one normally open momentary contact type switch and at least one single pole single throw type switch.

18. An improved teething and cleaning apparatus, comprising:

a rigid interior member defining a handle and a tongue shaped portion;

a flexible outer jacket substantially surrounding and coupled to said interior member, said outer jacket sized to partially enter the mouth of a child;

a motor coupled to an offset and said interior member, said motor and offset producing vibrational forces;

a power source, said power source coupled to said interior member; and at least one normally open momentary contact electrical switch, said at least one switch coupled between said motor and said power source;

wherein, in use, said infant teethes on said outer jacket thereby closing said at least one momentary contact electrical switch which electrically connects said power source with said motor and offset which then produces vibrational forces which are transmitted throughout said interior member and said outer jacket.

19. The improved teething and cleaning apparatus as set forth in claim 18 further comprising:

a slide switch coupled between the motor and the power source.

* * * * *